(12) United States Patent
Snyder et al.

(10) Patent No.: US 6,692,526 B1
(45) Date of Patent: Feb. 17, 2004

(54) OPHTHALMOLOGICAL SURGERY COLORANT AND DELIVERY SYSTEM

(76) Inventors: Michael E. Snyder, 8561 Chaucer Pl., Cincinnati, OH (US) 45249; Robert J. Cionni, 11425 Grandstone La., Cincinnati, OH (US) 45249; Scott E. Burk, 106 Winding Way, Covington, KY (US) 41011

(*) Notice: Subject to any disclaimer, the term of this patent is extended or adjusted under 35 U.S.C. 154(b) by 0 days.

(21) Appl. No.: 09/525,962

(22) Filed: Mar. 15, 2000

(51) Int. Cl.$^7$ ................................................. A61F 2/16
(52) U.S. Cl. .................. 623/6.63; 623/905; 606/4; 606/107; 604/19; 128/898
(58) Field of Search ..................... 623/6.63, 905; 606/107, 4; 604/19; 128/898

(56) References Cited

U.S. PATENT DOCUMENTS

| | | | |
|---|---|---|---|
| 5,279,298 A | | 1/1994 | Flower |
| 5,377,686 A | | 1/1995 | O'Rourke et al. |
| 5,569,191 A | * | 10/1996 | Meyer .................... 604/82 |
| 5,576,013 A | | 11/1996 | Williams et al. |
| 5,804,448 A | | 9/1998 | Wang et al. |
| 6,367,480 B1 | * | 4/2002 | Coroneo ................... 623/6.11 |
| 6,372,449 B1 | * | 4/2002 | Coroneo ................... 435/40.5 |
| 6,533,769 B2 | * | 3/2003 | Holmén ..................... 604/521 |

FOREIGN PATENT DOCUMENTS

| | | | | |
|---|---|---|---|---|
| WO | WO 99/58159 A1 | * | 11/1999 | .......... A61K/49/00 |
| WO | WO 99/58160 A1 | * | 11/1999 | .......... A61K/49/00 |

OTHER PUBLICATIONS

Kadonosono et al. Staining of internal limiting membrane in macular hole sugery. Arch Ophthalmology, 2000; 118:1116–1118.*

Desroches, G. Indocyanine Green Staining of the Internal Limiting Membrane. www.occojournal.com. 2001.*

Mester, Viktoria and Kuhn, Ferenc, "Internal Limiting Membrane Removal in the Management of Full–Thickness Macular Holes," Am. J. of Ophthalmology, Elsevier Science Inc., vol. 129, No. 6, pp. 769–777, (2000).

Fine, BS, "Limiting Membranes of the Sensory Retina and Pigment Epithelium: An Electron Microscopic Study", Arch Ophthalmol, vol. 66, pp. 847–860, (1961).

Clarkson JG, Green WR, Massof D., "A Histopathologic Review of 168 Cases of Preretinal Membrane," Am. J. Ophthalmol, vol. 84, No. 1, pp. 1–17, (1977).

Michels RG, "A Clinical and Histopathologic Study of Epiretinal Membranes Affecting the Macula and Removed by Vitreous Surgery," Tr Am Ophthalmol Soc, vol. LXXX pp. 580–656, (1982).

Smiddy WE, Green WRR, Michels RG, De La Cruz Z, "Ultrastructural Studies of Vitreomacular Traction Syndrome," Am. J. Ophthalmol, Vo. 107, No. 2, pp. 177–185, (1989).

Smiddy WE, Michels RG, De Bustros S, et al., "Histopathology of Tissue Removed During Vitrectomy for Impending Macular Holes," vol. 108, No. 4, Am. J. Ophthalmol, p. 360–364, (1989).

Smiddy WE, Michels RG, Green WR., "Morphology, Pathlogy and Surgery of Idiopathic Vitreoretinal Disorders. A Review," Retina, vol. 10, No. 4, pp. 288–296, (1990).

Guyer, DR, Green WR, De Bustros S, Fine SL, "Histopathologic Features of Idiopathic Macular Holes and Cysts," Ophthalmology, vol. 97, No. 8, pp. 1045–1051, (1990).

(List continued on next page.)

Primary Examiner—David H. Willse
Assistant Examiner—Javier G. Blanco
(74) Attorney, Agent, or Firm—Dobrusin & Thennisch PC

(57) ABSTRACT

Improved ophthalmological surgical methods, systems and devices, employing a colorant.

6 Claims, 2 Drawing Sheets

OTHER PUBLICATIONS

Zarbin MA, Michels RG, Green WR, "Epiretinal Membrane Contracture Associated with Macular Prolapse," Am J Ophthalmol, vol. 110, No. 6, pp. 610–618, (1990).

Park DW, Sipperley JO, Sneed SR, et al., "Macular Hole Surgery With Internal–Limiting Membrane Peeling and Intravitreous Air," Ophthalmology, vol. 106, No. 7, pp. 1392–1398, (1999).

Eckardt C., Eckardt U, Groos S, et al., "Removal of the Internal Limiting Membrane in Macular Holes," Ophthalomologe, p. 545–551, (1997).

Olsen TW, Sternberg P Jr, Capone A Jr, et al., "Macular Hole Surgery Using Thrombin–Activated Fibrinogen and Selective Removal of the Internal Limited Membrane," Retina, vol. 18, No. 4, pp. 322–329, (1998).

Yoon HS, Brooks HL, Jr., Capone A Jr., et al., "Ultrastructural Features of Tissue Removed During Idiopathic Macular Hold Surgery," Am J Opthalmol, vol. 122, No. 1, pp. 67–75, (1996).

Maguire AM, Smiddy WE, Nanda SK et al., "Clinicopathologic Correlation of Recurrent Epiretinal Membranes After Previous Surgical Removal," Retina, vol. 10, No. 3, pp. 213–222, (1990).

Hope–Ross M, Yannuzzi LA, Gragoudas ES, et al., "Adverse Reactions Due to Indocyanine Green," Ophthalmology, vol. 101, No. 3, pp. 529–533 (1994).

Destro M, Puliafito CA, "Indocyanine Green Videoangiography of Choroidal Neovascularization," Ophthalmology, vol. 96, No. 6, pp. 846–853, (1989).

Yannuzzi LA, Slakter JS, Sorenson JA et al., "Digital Indocyanine Green Videoangiography and Choridal Neovascularization," Retina, vol. 12, No. 3, pp. 191–223, (1992).

Guyer DR, Puliafito CA, Mones JM, et al., "Digital Indocyanine–Green Angiography in Chorioretinal Disorders," Ophthalmology, vol. 99, No. 2, pp. 287–291, (1992).

Ho AC, Yannuzzi LA, Guyer DR, et al., "Intraretinal Leakage of Indocyanine Green Dye," Ophthalmology, vol. 101, No. 3, pp. 534–541, (1994).

McEnerney JK, Peyman GA, "Indocyanine Green: A New Viral Stain for Use Before Penetrating Keratoplasty," Arch Ophthalmol, vol. 96, pp. 1445–1447, (1978).

Horiguchi M, Miyake K, Ohta I, Ito Y, "Staining of the Lens Capsule for Circular Continous Capsulorrheix in Eyes with White Cataract," Arch Ophthalmol, vol. 116, p. 535–537, (1998).

Smiddy, WE (Discussion by)–Park DW, Sipperley JO, Sneed SR et al., "Macular Hole Surgery with Internal–Limiting Membrane Peeling and Intravitreous Air," Ophthalmology, vol. 106, No. 7, pp. 1397–1398, (1999).

Erza E, Aylward WG, Gregor ZJ, "Membranectomy and Autologous Serum for the Retreatment of Full–Thickness Macular Holes," Arch Ophthalmol, vol. 115, pp. 1276–1280, (1997).

Ferris JD, "Pathogenesis of Idiopathicmacular Holes," Current Opin Ophthalmol, vol. 8, pp. 87–93, (1997).

Weingeist TA, Goldman EJ, Folk JC et al., "Terson's Syndrome. Clinicopathologic Correlations," Ophthalmogy, vol. 93, No. 11, pp. 1435–1442, (1986).

Russell SR, Hageman GS, "Hemorhagic Detachment of the Internal Limiting Membrane After Penetrating Ocular Injury," Retina, vol. 12, No. 4, pp. 346–350, (1992).

Livingstone, BI, Bourke, RD, "A Retrospective Study of Macular Holes with Pars Plana Vitrectomy Aust NZ J Ophthalmol," 1999; in press.

Lutty, GA., "The Acute Intravenous Toxicity of Biological Stains, Dyes and Other Fluorescent Substances," Toxicol Appl Pharmacol, 44: 225–249 (1978).

Friedman, Scott M. and Margo, Curtis E., "Bilateral Sub-internal Limiting Membrane Hemorrhage with Terson Syndrome," Am. J. of Ophthalmology, vol. 124, No. 6, pp. 850–851 (1997).

Foos FY, "Vitreoretinal Juncture: Topographical Variations," Invest Ophthalmol, vol. 11, pp. 801–808 (1972).

Russell SR, Shepherd JD, Hageman GS, "Distribution of Glycoconjugates in the Human Retinal Internal Limiting Membrane," Invest Ophthalmol Vis. Sci., vol. 32, pp. 1986–1995 (1991).

Burk, Scott E., MD, PhD, Snyder, Michael E., MD; Cionni, Robert J., MD; Osher, Robert H., MD, Journal of Cataract Refractive Surgery, vol. 25, No. 6, pp. 1–9 (Jun. 1999).

* cited by examiner

OPHTHALMOLOGICAL SURGERY COLORANT AND DELIVERY SYSTEM

TECHNICAL FIELD

The present invention relates generally to the field of biocompatible fluid delivery for ophthalmologic surgery, and more particularly relates to staining for enhanced performance in ophthalmological surgical procedures involving the removal of materials from the eye.

BACKGROUND OF THE INVENTION

It is often desirable in the surgical field, and particularly in the field of microsurgery, such as ophthalmological surgery, to introduce stains, dyes or colorants (referred to collectively as "colorant") into a surgical site of a patient in order to enhance visual detail of the site. A suitable colorant must be biocompatible with the patient. For instance, it must be generally nontoxic and exhibit a pH compatible with the patient. Moreover, it must exhibit sufficient viscosity, surface and wetting characteristics so that it can be suitably directed to the region of interest, upon being administered to the patient.

A number of commercially available biocompatible colorants exist in the medical field, as the skilled artisan will appreciate. Without limitation, an example of one type of colorant that has attracted attention for certain applications is indocyanine green. That colorant has been used successfully in certain procedures, such as retinal angiograms, and other imaging studies of organs, owing largely to its ability to fluoresce, such as upon being suitably excited from an external energy source. U.S. Pat. No. 5,804,448 (Wang, et al); U.S. Pat. No. 5,576,013 (Williams, et al); U.S. Pat. No. 5,377,686 (O'Rourke et al); and U.S. Pat. No. 5,279,298 (Flower), all of which are expressly incorporated by reference herein.

Only recently has it been suggested that indocyanine green be used as an adjunct to cataract surgery to aid in visualizing the anterior capsule (the clear "front" membrane that encases the cloudy natural lens or "cataract"), in certain special cases where the anterior capsule is otherwise difficult to resolve optically. Though other colorants have been attempted for limited use in cataract surgery, the use of such colorants (for cataract surgery or other ophthalmological surgical procedures) still remains largely unexplored. Consequently, efficacy and other biocompatibility data is lacking or is dubious, i.e., is limited to highly specific conditions.

Moreover, it is believed that the use of a colorant such as indocyanine green has never been attempted for retinal surgery procedures. Recently, surgical removal or peeling of the internal-limiting membrane ("ILM") has been described as a potentially useful adjunct to vitreoretinal surgery, particularly in select macular hole cases, or other disorders characterized by an abnormal vitreoretinal interface. Typically, when the ILM is peeled, there are only subtle visible clues if any to determine the location of the border between unpeeled ILM and adjacent underlying retina or to define the best edge for continued peeling of the ILM. For example, where the ILM has been peeled, the underlying retina often acquires a rough or dull sheen, and there are often small intraretinal hemorrhages within the peeled area. However, it may be difficult to initiate the ILM peel and to visualize the border or edge of the membrane once ILM peeling has been started. It may also be difficult to continue an ILM peel if the edge is lost, or to determine the total extent of a peel (including from prior operations). Thus, difficult visualization of the ILM as well as firm attachment of the ILM to the underlying layers of the retina present potential technical challenges when trying to peel this membrane.

Ophthalmological surgery poses other unique constraints on the successful use of colorants to aid optical resolution. For example, the necessary tonicity of the colorant and any carrier that is used to deliver the colorant to the eye requires precise control over the composition and concentration of the colorant/carrier admixture. Some commercially available components for the admixture are provided as two-component systems (e.g., a granular precipitate and a solvent) that must be mixed in suitable proportions before administering to the patient. Moreover, the colorant systems typically have a relatively short shelf-life (e.g., commercially available indocyanine green commonly is marketed as having a fluorescence stability of only about 10 hours upon mixing).

References of potential interest to the present invention, all of which are expressly incorporated by reference, include:

Fine, B S. Limiting membranes of the sensory retina and pigment epithelium: an electron microscopic study. Arch Ophthalmol 1961;66:847–60.

Clarkson J G, Green W R, Massof D. A histopathologic review of 168 cases of preretinal membrane. Am J Ophthalmol 1977;84:1–17.

Michels R G. A clinical and histopathologic study of epiretinal membranes affecting the macula and removed by vitreous surgery. Tr Am Ophthalmol Soc 1982;80:580–656.

Smiddy W E, Green W R, Michels R G, de la Cruz Z. Ultrastructural studies of vitreomacular traction syndrome. Am J Ophthalmol 1989;107:177–85.

Smiddy W E, Michels R G, de Bustros S, et al. Histopathology of tissue removed during vitrectomy for impending macular holes. Am J Ophthalmol 1989;108:360–4.

Smiddy W E, Michels R G, Green W R. Morphology, pathology, and surgery of idiopathic vitreoretinal disorders. A review. Retina 1990;10:288–296.

Guyer D R, Green W R, de Bustros S, Fine S L. Histopathologic features of idiopathic macular holes and cysts. Ophthalmology 1990;97:1045–51.

Zarbin M A, Michels R G, Green W R. Epiretinal membrane contracture associated with macular prolapse. Am J Ophthalmol 1990;110:610–8.

Park D W, Sipperley J O, Sneed S R, et al. Macular hole surgery with internal-limiting membrane peeling and intravitreous air. Ophthalmology 1999;106:1392–8.

Eckardt C, Eckardt U, Groos S, et al. Removal of the internal limiting membrane in macular holes. Ophthalmologe 1997;94:545–51.

Olsen T W, Sternberg P Jr, Capone A Jr, et al. Macular hole surgery using thrombin-activated fibrinogen and selective removal of the internal limiting membrane. Retina 1998;18:322–9.

Yoon H S, Brooks H L, Jr, capone A Jr, et al. Ultrastructural features of tissue removed during idiopathic macular hole surgery. Am J Ophthalmol 1996;122:67–75.

Maguire A M, Smiddy W E, Nanda S K, et al. Clinicopathologic correlation of recurrent epiretinal membranes after previous surgical removal. Retina 1990;10:213–22.

Livingstone, B I, Bourke, R D. A retrospective study of macular holes with pars plana vitrectomy. Aust NZ J Ophthalmol 1999; in press.

Hope-Ross M, Yannuzzi L A, Gragoudas E S, et al. Adverse reactions due to indocyanine green. Ophthalmology 1994; 101:529–33.

Lutty G A. The acute intravenous toxicity of biological stains, dyes, and other fluorescent substances. Toxicol Appl Pharmacol 1978;44:225–49.

Destro M, Puliafito C A. Indocyanine green videoangiography of choroidal neovascularization. Ophthalmology 1989;96:846–53.

Yannuzzi L A, Slakter J S, Sorenson J A, et al. Digital indocyanine green videoangiography and choridal neovascularization. Retina 1992;12:191–223.

Guyer D r, Puliafito C A, Mones J M, et al. Digital indocyanine-green angiography in chorioretinal disorders. Ophthalmology 1992;99:287–91.

Ho A C, Yannuzzi L A, Guyer D R, et al. Intraretinal leakage of indocyanine green dye. Ophthalmology 1994;101:534–41.

McEnerney J K, Peyman G A. Indocyanine green: a new vital stain for use before penetrating keratoplasty. Arch Ophthalmol 1978;96:1445–7.

Horiguchi M, Miyake K, Ohta I, Ito Y. Staining of the lens capsule for circular continuous capsulorrhexis in eyes with white cataract. Arch Ophthalmol 1998;116:535–7.

Smiddy W E. Discussion of: Park D W, Sipperley J O, Sneed S R, et al. Macular hole surgery with internal-limiting membrane peeling and intravitreous air. Ophthalmology 1999;106:1397–8.

Erza E, Aylward W G, Gregor Z J. Membranectomy and autologous serum for the retreatment of full-thickness macular holes. Arch Ophthalmol 1997;115:1276–80.

Ferris J D. Pathogenesis of idiopathicmacular holes. Current Opin Ophthalmol. 1997;8:87–93.

Weingeist T A, Goldman E J, Folk J C, et al. Terson's syndrome. Clinicopathologic correlations. Ophthalomogy 1986;93:1435–42.

Russell S R, Hageman G S. Hemorrhagic detachment of the internal limiting membrane after penetrating ocular injury. Retina 1992;12:346–50.

Friedman S M, Margo C E. Bilateral subinternal limiting membrane hemorrhage with Terson syndrome. Am J Ophthalmol 1997;124:850–1.

SUMMARY OF THE INVENTION

The present invention constitutes a substantial improvement in the surgical field, particularly in the ophthalmological surgical field. In accordance with the methods, devices, and systems of the present invention, there is provided an improved delivery vehicle for the administration of a biocompatible colorant into a surgical region of a patient. Generally, the methods of the present invention contemplate the steps of admixing at least two separate components to provide a colorant admixture for improving the optical resolution for a surgeon of a surgical region of a patient, and administering the admixture to the patient. In a particularly preferred embodiment, a cataract removal is performed on the patient followed by the implantation of an intraocular lens (IOL). In another particularly preferred embodiment, a thin layer the retina is removed.

The devices of the present invention generally include at least a first chamber for containing a first component of the colorant admixture and a second chamber for containing a second component of the colorant admixture. The first and second components are admixed in a third chamber (which may or may not include the first and second chambers). In one embodiment, the devices also are adapted to be in fluid communication with a suitable instrument for transferring the admixture from the device and into the surgical region.

In a particularly preferred embodiment, the colorant admixture includes indocyanine green in a sterile liquid solvent, and is provided in a container initially having two or more chambers. For instance, the solvent is provided in a first chamber, and the colorant is provided as a solid (e.g., freeze dried crystals) in a second chamber adjoining the first chamber and separated therefrom by a displaceable wall. Alternatively, the colorant is in liquid medium and may be provided in a single chamber container. The admixture is used for an ophthalmological surgical procedure, such as cataract or retinal surgery, where it provides a contrast medium (with or without fluorescence) for improving the optical resolution of the surgical region. During surgery, the wall is displaced and a third chamber effectively is created (which may include at least a portion of the first or second chambers), and the first and second components are admixed in the third chamber.

The present invention offers a number of significant advantages over the prior art. For example, without limitation, the present invention can be used in various surgical procedures heretofore not employed, such as cataract or retinal surgery, in order to improve the optical viewing characteristics and resolution of the surgical region. The present invention also permits for the administration of controlled doses of a colorant admixture, with insignificant waste of the admixture component (many of which typically are expensive and have relatively short shelf-lives), thereby reducing wasted colorant admixture and also allowing surgeons improved control over the concentration and dosage amounts of the admixture.

DETAILED DESCRIPTION OF THE PREFERRED EMBODIMENTS

Figure 1:
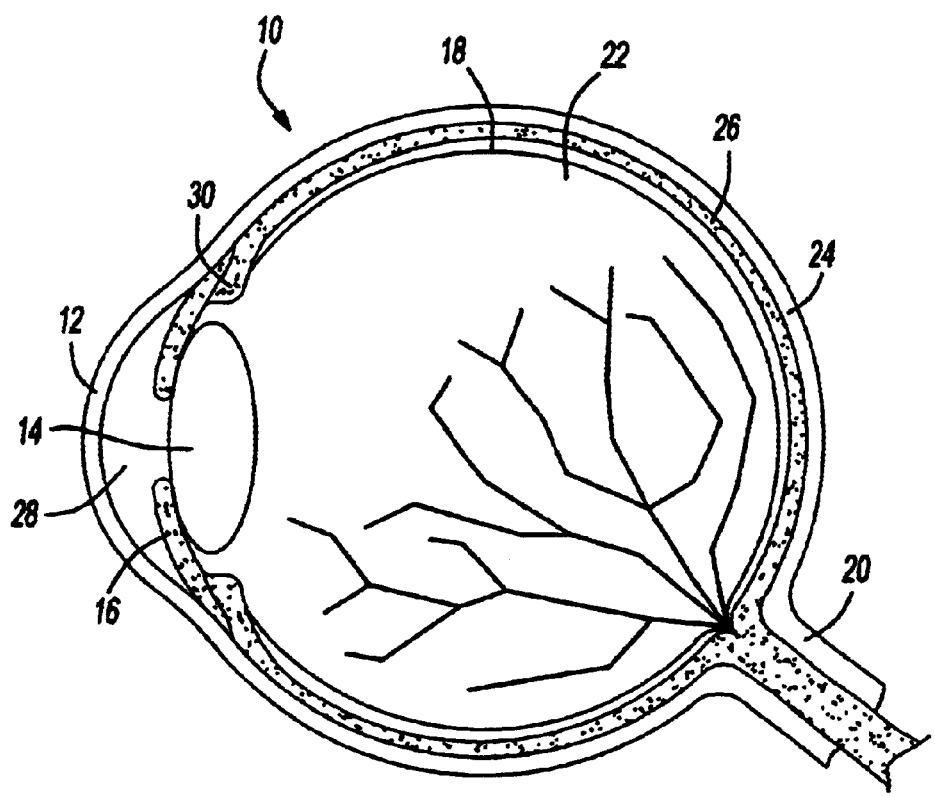
FIG. 1 is a schematic section of a human eye.
Figure 2:
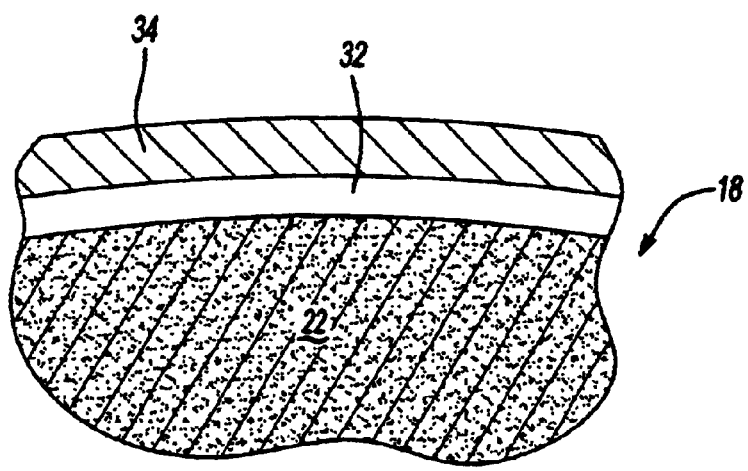
FIG. 2 is a sectional view of the vitreous and retina interface.

The skilled artisan will be familiar with the anatomy of a human eye. By way of brief review, FIG. 1 illustrates a section of a human eye 10. The eye includes a cornea 12, a lens capsule 14 and an iris 16 between the cornea and lens. A multi-layer retina 18 lines a back portion of the interior of the eye, and senses light, sending impulses to the brain through an optic nerve 20, toward the back or posterior portion of the eye. A jelly-like substance or vitreous 22 is comprised within the eye. A sclera layer 24 is shown adjacent a choroid 26. A pupil 28 is defined in the opening of the iris 16. Ciliary body 30 is behind the iris. As seen in FIG. 2, retinal internal-limiting membrane (ILM) 32 forms a structural boundary in the retina 18, with vitreous 22. It is derived mostly from the basement membrane elaborated by footplates of Müller cells, with vitreous fibrils contributing to the inner portion of the ILM. As a basement membrane ILM can act as a scaffold for cellular proliferation and is frequently involved in disorders that affect the vitreomacular interface, including epiretinal membranes, vitreomacular traction, and macular holes.

Figure 3:
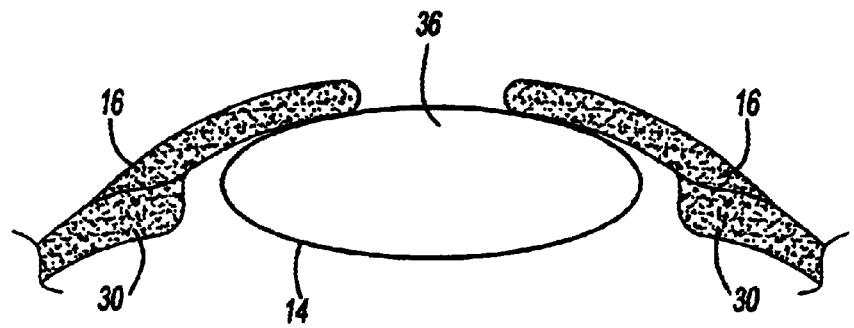
FIG. 3 is a sectional view of a lens capsule.

Referring to FIG. 3 a cataract is a condition in which an opacity of the usually clear natural lens develops within the anterior chamber 36 of the lens capsule 14. The opacity effectively causes blurring, fogging or other distortion of images.

In the methods of the present invention, the skilled artisan will appreciate that any suitable technique may be employed for removal of a cataract, including extracapsular surgery or phacoemulsification. Preferably, the well known phacoemulsification method may be used. In general, for instance, that method contemplates that an incision is made in the anterior portion of the lens capsule. The incision is of sufficient size that it permits ingress and egress of surgical instruments into the lens capsule of the eye, in which the cataract material is located. After incision, the surgeon will typically insert an instrument and cut, scrape, vibrate (e.g., ultrasonic) or otherwise induce the central core or nucleus of the cataract to soften or break-up into smaller (preferably microscopic) pieces that can be removed. Removal of the pieces of the broken up cataract is continued using well known suction or phaco-emulsification techniques until substantially the entirety of the cataract is removed from the lens capsule. The same or another probe may be used to remove the cortex, preferably by suction. Thereafter, the capsule is further prepared (e.g., vacuumed and polished) and a suitable intraocular lens may be implanted within the anterior capsule. The posterior portion of the lens capsule remains.

Likewise, the skilled artisan will appreciate that any suitable technique may be employed to remove or "peel" the ILM 32 of the retina from the eye. In general, for instance, a suitable incision is made to provide ingress and egress of surgical instruments to the regions adjacent the ILM. A suitable instrument is inserted into the eye, and is moved into contacting relationship with the ILM. The instrument preferably is brought into direct contact with the layer. The layer is abraded, strained or otherwise manipulated until at least a portion of the innermost layer is raised or loosened so that it can be engaged (e.g., gripping or vacuum) by a suitable instrument, and while so engaged, peeled from the retina. Suitable cutting instruments may be employed as well to facilitate the peel process. The peel is accomplished in either a single step or in a plurality of consecutive steps. Preferably the entirety of the layer is removed, leaving only the underlying retina portion 34, as seen in FIG. 2. These techniques may also be employed to remove other layers (e.g., an epiretinal membrane layer) that are disposed on an ILM or on another retinal surface.

In one embodiment, the thickness of the layers removed is less than about 10 micrometers. In another, it is less than about 5 micrometers.

The present invention contemplates facilitating the ophthalmological surgical procedures of the present invention by introducing into the eye a colorant, and more preferably one that provides a contrast between adjacent surfaces (and more preferably adjacent layers or membranes) within the eye. In turn, the surgeon is able to more readily visually distinguish between the such surfaces. By way of example, the present colorant may be employed selectively to help distinguish between two or more contiguous surfaces that lie one on top of the other over at least a portion of their surfaces. Likewise, the colorant may be used to distinguish between two or more regions of the eye that lie within the same general curved surface or plane. By way of example, for a cataract surgery procedure, the anterior capsule is stained, but not the cataract itself. Moreover, for the retinal peel procedure, the ILM 32 or innermost layer is stained, but preferably not the underlying retina portion 34. In this manner, the surgeon is able to readily determine when the material to be removed has been removed from the surgical site. Moreover, particularly for retina peels, the colorant allows the surgeon to visually distinguish between the layer to be removed, and other portions of the eye, such as the retina that remains, the macula, the veins and the arteries.

The colorant of the present invention may be any suitable biocompatible dye, stain or other colorant. Preferably, the colorant is sufficient for localized staining and for staining to controlled depths within layers of the eye, thereby permitting the colorant to be selectively and controllaby introduced into the surgical region. The color of the colorant may vary from procedure to procedure, but preferably it is sufficient to allow a surgeon to visibly distinguish between layers or regions in the eye by virtue of the appearance of a contrast between colored regions and regions that are not colored. Further, it is preferred that the color be sufficiently distinct from and in contrast with other adjacent cells or anatomy within the eye. The colorant should generally be nontoxic to the patient in the appropriate dosage. Further, it is preferable that the colorant have a half life that is of sufficient duration so that the surgical procedure can be completed while the colorant remains effective as a contrasting agent, but will not substantially impair the sight of the patient upon healing from the procedure. It is also preferred that the colorant bind avidly to protein, but is sufficiently hydrophilic so that it tends to be excluded from living cells by intact cell membranes.

In accordance with the above, it being recognized that any of a number of different colorants may be employed, a preferred colorant is one that has blue tones, green tones or a mixture thereof. In one embodiment, the colorant exhibits fluorescent properties such that upon excitation by a suitable energy source (e.g., a laser), the colorant will fluoresce to provide a contrast with adjacent regions. A particularly preferred colorant for use in the present invention is known in the art as indocyanine green. Specific examples of other colorants include, without limitation, trypan blue, toluidine blue, methylene blue, gentian violet, and fluorescein. One unique feature of the indocyanine green colorant of the present invention is its ability to provide relative good contrast characteristics beyond its stable fluorescence life. Thus, for example, an indocyanine green colorant that has been exposed to air, room temperature, and lighted atmospheric conditions still exhibits satisfactory contrast characteristics at least 8 hours after exposure, 12 hours after exposure, 24 hours after exposure, 2 days after exposure, 3 days after exposure, one week after exposure, two weeks after exposure, three weeks after exposure, one month after exposure, or longer. Thus, it is contemplated that any admixture employing indocyanine green may be administered after the period of recommended stable shelf life.

Though it is contemplated that the colorant may be employed as a concentrate, more preferably it is diluted or otherwise treated sufficiently for introduction into the eye with inconsequential patient response, but for the contrast induced. Accordingly, the colorant is prepared so that it exhibits a pH ranging from about 6 to about 8, and more preferably about 7.

Moreover, the osmolarity is such that the colorant is delivered only to the desired region of the eye, and excess colorant transport across a membrane or layer in the eye is avoided. The osmolarity accordingly ranges from about 200 to about 325, more preferably about 250 to about 300, and still more preferably is about 270 mOsm.

The colorant may be delivered to the eye in any of a number of suitable ways, including but not limited to by dropper, swabbing, injection, spraying, brushing, rolling or the like. The manner in which the colorant is added typically will determine whether and how the colorant should be dispersed or otherwise placed in a fluid (e.g., liquid) delivery medium as needed for delivery. By way of example, in most applications, it is contemplated that the fluid delivery medium will be a liquid and the colorant will be administered into the eye via an admixture including the delivery medium and the colorant. Moreover, in many such applications, it is contemplated that a conduit having a open end (e.g., a dropper or a hollow needle will be employed for directing the admixture toward the specific surgical region to be colored. The diameter of the open end of the conduit will be very small (e.g., a syringe canula having a bore of about 20 to about 40 gauge, and more preferably about 25 to 30 guage). Thus, it is necessary for the admixture to exhibit sufficient fluidity or viscosity characteristics so that it will pass through the open end of the conduit with relatively insignificant shear or frictional resistance that would otherwise generate energy or raise the temperature of the admixture undesirably.

It will be recognized by the skilled artisan that the surface free energy characteristics of the liquid of a liquid colorant admixture and its associated properties can be varied and modified as desired to achieve the desired characteristics, such as wetting or the like. In this regard the colorant admixture may include any of a number of modifiers, such as surfactants. Other ingredients may also be added as desired to tune the properties for a specific application. Examples of additives include, for instance, antibiotics, buffers, or viscous agents such as hyaluronic acid, chondroitin sulfate, methyl cellulose, dextran, or the like.

In one preferred embodiment, the colorant is provided in a concentrated state and is diluted prior to or during administration to the patient. Thus, systems of the present invention contemplate a method, device or both for admixing the colorant with a diluent that serves as a liquid delivery medium. Preferably, the diluent is a sterile aqueous solution, and further includes a salt. In one preferred embodiment, the diluent is an iso-osmotic diluent. It is possible to prepare the colorant admixture prior to or during administration to the patient. For instance, diluent and colorant can be provided from two separate containers and brought into mixing contact with each other outside of their respective containers. Mixing can also be done by bringing the componenets into one common container or location. It is possible to prepare the colorant admixture prior to or during administration to the patient. For instance, diluent and colorant can be provided from two separate containers and brought into mixing contact with each other outside of their respective containers. Mixing can also be done by bringing the components into one common container or location.

Figure 4:
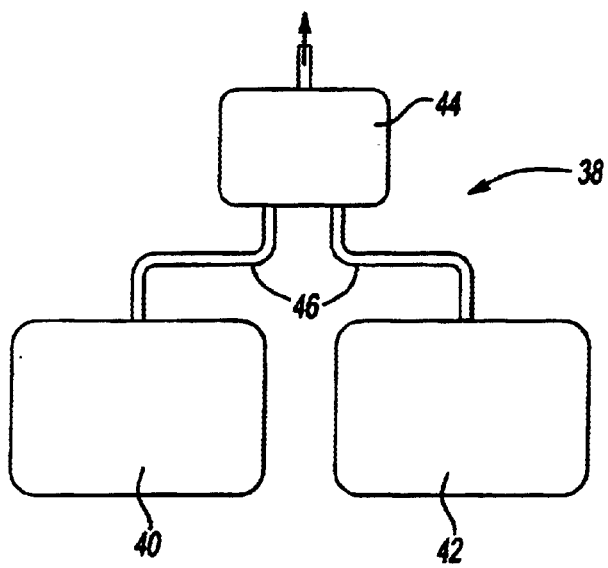
FIG. 4 is a schematic of a multiple chamber mixing device in accordance with the present invention.

By way of example, by reference to FIG. 4, colorant can be provided in a first receptacle 40 and diluent in a container system 38 having second receptacle 42. They can be pumped, drawn other otherwise transported to a third receptacle 44, which is external of both the first and second receptacle. The third receptacle 44 preferably is in fluid communication with a conduit (e.g., a hollow needle), nozzle or other suitable delivery instrument (not shown), having an opening through which fluid can pass into the patient. The skilled artisan will appreciate that various adaptations of such an arrangement are possible. Moreover, the device can be modified to permit more than two components to be mixed. It can also be adapted to receive applicator attachments (including disposable and nondisposable applicators) suitable for swabbing or spreading the colorant. Mixing of colorant and diluent can occur in the first receptacle, the second receptacle or the third receptacle.

Figure 5:
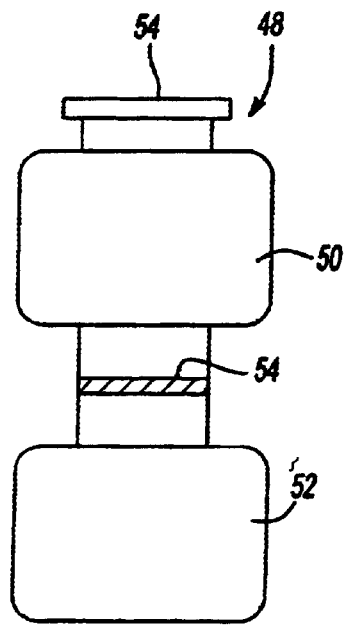
FIG. 5 is a schematic of another multiple chamber mixing device in accordance with the present invention.

In another preferred embodiment, referring to FIG. 5, the components of the colorant admixture are provided as a single unit 48, which contains a plurality of chambers (e.g., 50 and 52) for separating the components at the outset, and an opening 54 through which dispensing is possible. However, at least one wall or barrier divides the unit into chambers, and is displaceable relative to the chambers, to permit components to mix with each other. By way of illustration, in one embodiment, a rupturable membrane or moveable barrier separates two or more chambers. In use the membrane can be ruptured or the barrier moved to permit intermixing of the components effectively in an in situ created mixing chamber that includes chambers 50, 52 or both. The separating partition need not be limited to a rupturable membrane, and may suitably include a hinged door or flap, a sliding door, a collapsible wall (e.g., by squeezing the unit), or any other like structure that will permit at least a portion of the wall to be displaced and allow mixing of contents of the respective chambers.

Without limitation, one example of one suitable system is that used by Ciba-Geigy for dispensing its Miochol product.

Of course, it is also within the scope of the present invention to have premixed colorant admixtures provided in a single container in a suitable dosage amount (e.g., not exceeding about 2 cc, more preferably, not exceeding about 1 cc and preferably about 0.5 cc) or in larger or smaller amounts. Further, prior to administration to a patient the components of the admixture can be mixed manually (e.g., by pipetting appropriate respective amounts into a beaker or vial).

Following a suitable time after administering the colorant to the patient excess colorant is removed, such as by suctioning it from the eye.

It will be appreciated that the present invention affords a number of unique advantages, including the ability to provided in metered dosage amounts a medicinal or biocompatible material having multiple starting components that must be kept separated until shortly before administration to a patient. In a highly preferred embodiment, the colorant admixture includes indocyanine green. It is provided as a two component set of starting materials, specifically, indocyanine green particles (e.g., crystals, or other freeze-dried precipitates) as one, and a diluent as the other. An aliquot having a volume (approximating the total dosage amount) of about 0.5 cc and the structure of the embodiment of FIG. 5 is filled with the respective starting materials (e.g., about 1 to about 4 mg of colorant and about 0.5 ml of a diluent). The membrane or wall is displaced just prior to administration to a patient. For ophthalmological procedures, such as the aforenoted cataract removal surgery or the retinal peel, the colorant is injected into the eye through a hollow needle an brought into staining contact with the layer in the eye for which staining is desired.

If fluorescing is desired than a suitable excitation energy source is provided (e.g., a laser), is directed toward the colorant during the fluorescent half life of the colorant. If fluorescing is not desired, it is possible to admix the components of the colorant admixture days, weeks or months in advance of the procedure, and successful results are possible.

EXAMPLE 1

About 25 mg of sterile ICG powder (e.g., IC-GREEN™, Akorn, Inc, Buffalo Grove, Ill.) is dissolved in about 0.5 ml of sterile aqueous solvent. The mixture is shaken for approximately 5 minutes until there is a homogenous green solution without any visible particles. About 4.5 ml of sterile balanced salt solution is added to produce a solution with a final ICG concentration of 0.5% and osmolarity of 270 mOsm.

Human cadaveric eyes are examined in the laboratory to determine if the ICG solution stains the retinal ILM. The entire anterior segment of the eye is excised to gain access to the vitreous cavity. Following open sky vitrectomy, 0.3 ml of ICG solution is injected through a 5 micron filter into the posterior vitreous cavity over the macula. The dye is left in place on the macula for 5 minutes. The ICG is then removed by mechanical aspiration leaving the stained ILM clearly visible as characterized by a bright green color. A bent 22 g needle is used to create the initial ILM tear. Intraocular foreign body forceps are then used to grasp the elevated ILM edge. The ILM is peeled in a continuous, circular manner similar to a capsulorhexis in cataract surgery. In each case, the ILM peel removes 3 to 4 disc diameters of ILM centered approximately on the fovea. Peeled ILM and cadaver eyes are fixed in 10% buffered formalin for histopathologic preparation. Specimens are evaluated by light microscopy.

After the ICG is removed, the green staining of the ILM improves the ability to initiate the peel because when the needle penetrated through the ILM, the unstained underlying retina is more readily apparent. The flap of ILM is easily seen and grasped with intraocular forceps and the distinct contrast between the stained ILM and the unstained retina facilitates the continuation of ILM peeling.

The posterior hyaloid remains attached following limited open sky vitrectomy. Examination under the operating microscope demonstrates that the posterior cortical vitreous contains a small amount of trapped ICG, which assists in identifying and stripping the posterior cortical hyaloid. Following removal of the posterior cortical vitreous, less staining of the underlying ILM is observed than in the globes in which the posterior cortical vitreous are removed prior to ICG injection.

The peeled ILM and sectioned globes are submitted for histopathologic evaluation and electron microscopy. Periodic acid-Schiff (PAS) stain is used to identify the ILM. Light microscopic examination of the peeled membrane demonstrates a section of ILM with characteristic PAS-positive staining and typical sinusoidal folding. Light microscopic examination of the retina from the sectioned globes demonstrated in situ PAS-positive ILM in the peripheral macula, with an abrupt absence of ILM in the central macula where it is peeled.

EXAMPLE 2

The procedures of Example are followed using human patients having macular holes, epiretinal membrances, or both. Successful peeling of the ILM, the epiretinal membrane or both is achieved using indocyanine green staining.

What is claimed is:

1. A method for improving optical resolution of an ophthalmological surgical region of a patient, comprising the steps of:
   a) administering indocyanine green into the retinal portion of an eye of the patient for increasing the contrast of constituent portions of the surgical region; and
   b) conducting a retinal peel on said eye.

2. The method of claim 1 wherein said indocyanine green admixture is administered to a patient after the period of its recommended stable fluorescence shelf life as an admixture.

3. The method of claim 1 wherein said indocyanine green is dissolved in a diluent.

4. The method of claim 1 wherein said indocyanine green is dissolved in an iso-osmotic diluent.

5. A method for removing a layer of material from an eye, comprising the steps of:
   a) providing a colorant admixture including:
      i) indocyanine green; and
      ii) a diluent;
   b) administering said colorant admixture into an eye of a patient;
   c) staining an inner layer of the retina in said eye; and
   d) peeling said inner layer to remove it from said eye.

6. The method of claim 5 wherein said colorant admixture is administered to a patient after the period of its recommended stable fluorescence shelf life as an admixture.

* * * * *